(12) United States Patent
De Polo et al.

(10) Patent No.: US 7,931,620 B2
(45) Date of Patent: Apr. 26, 2011

(54) SELF-SEALING CONNECTION FOR HOUSING SHELLS OF AN ADMINISTERING DEVICE

(75) Inventors: Marco De Polo, San Mateo, CA (US); Philip Etter, Ittigen (CH); Remo Steiner, Muenchenbuchsee (CH)

(73) Assignee: Roche Diagnostics International AG, Steinhausen (CH)

( * ) Notice: Subject to any disclaimer, the term of this patent is extended or adjusted under 35 U.S.C. 154(b) by 1257 days.

(21) Appl. No.: 11/345,652

(22) Filed: Feb. 1, 2006

(65) Prior Publication Data

US 2007/0185450 A1   Aug. 9, 2007

(51) Int. Cl.
*A61M 37/00* (2006.01)
(52) U.S. Cl. ........................................ 604/131
(58) Field of Classification Search ........... 604/131–163
See application file for complete search history.

(56) References Cited

U.S. PATENT DOCUMENTS

| | | |
|---|---|---|
| 5,370,622 A | 12/1994 | Livingston et al. |
| 6,305,908 B1 | 10/2001 | Hermann et al. |
| 6,379,337 B1 * | 4/2002 | Mohammad M. B. B. S. .................... 604/195 |
| 6,423,035 B1 * | 7/2002 | Das et al. ...................... 604/155 |
| 6,485,465 B2 * | 11/2002 | Moberg et al. ................. 604/154 |
| 7,066,909 B1 * | 6/2006 | Peter et al. .................... 604/136 |
| 2001/0021822 A1 * | 9/2001 | Ayer ............................. 604/148 |
| 2004/0024364 A1 * | 2/2004 | Langley et al. ............... 604/187 |
| 2007/0176322 A1 * | 8/2007 | Etter et al. .................... 264/255 |
| 2007/0178776 A1 * | 8/2007 | Etter et al. .................... 439/877 |

FOREIGN PATENT DOCUMENTS

EP   0 991 440 B1   10/1998

* cited by examiner

*Primary Examiner* — Nicholas D Lucchesi
*Assistant Examiner* — Aarti B Berdichevsky
(74) *Attorney, Agent, or Firm* — Dinsmore & Shohl, LLP

(57) ABSTRACT

Administering device for infusing or injecting a product, comprising a housing (1, 2) with a first housing shell (1) and a second housing shell (2), a receiver (3) for the product formed in the housing (1, 2), a conveying mechanism (4) for conveying the product and a seal (10), which connects the housing shells (1, 2) to one another in a pressing contact rendering them watertight, which seal (10) is or has a sealing lip (13) which establishes the pressing contact with the first housing shell (1).

25 Claims, 4 Drawing Sheets

SELF-SEALING CONNECTION FOR HOUSING SHELLS OF AN ADMINISTERING DEVICE

The invention relates to an administering device for infusing or injecting a product, preferably a liquid medicament such as insulin, for example, and a method of producing a housing shell of the device.

In many applications for which administering devices are used, the demands placed on them in terms of water tightness are high. This is of particular importance in situations where drugs are self-administered, as is common practice in the case of treatment for diabetes, for example. In terms of their external dimensions, administering devices have now become so small that they can be carried in virtually every day to day situation, for example during sport, whilst showering and even in water. Under all circumstances, it must be possible to guarantee water tightness under the conditions which can be anticipated during the time leading to the expiry date, and administering devices are designed to be serviceable for several months or even years. Water tightness is problematic because the housings of administering devices are made from a number of parts, i.e. of several housing shells, and the housing shells have to be connected to one another to provide a watertight seal. Impact resistance and reliable process assembly are absolutely crucial if water tightness is to be guaranteed over a longer service life.

One known approach is to connect housing shells by means of ultrasound welding or to adhere them with adhesive or sealant. A disadvantage of such joints is that joints of this type are not resistant to impacts. The joints are not able to absorb impact energy to the desired degree.

Other joints that are more conducive to achieving impact resistance are self-sealing joints, such as those used in the form of O-ring seal systems. O-ring seal systems operate by compressing an elastic O-seal between surfaces of two parts which have to be tightly joined to one another, for example housing shells. The sealing force is predominantly generated by the operating pressure, i.e. by the ambient pressure. The sealing effect increases as the operating pressure rises. At low operating pressures, on the other hand, there is a risk that the sealing action will not be sufficient due to the lower pressing force. The sealing ring must therefore be mounted so that it is still able to deform to a sufficient degree at low operating pressure in order to guarantee a perfect seal as the operating pressure rises, but on the other hand already generates a surface pressure which is sufficient to produce a perfect seal at low operating pressure. The sealing effect is also impaired by manufacturing and fitting inaccuracies of the housing shells which have to be sealed relative to one another.

One objective of the invention is to improve the water tightness of a multi-part housing of an administering device comprising a multi-part housing.

An administering device of the type to which the invention relates comprises a housing, a receiver provided in the housing to accommodate a product to be administered and a conveying mechanism for conveying the product. The receiver for the product may be an actual product container itself. However, a container for the product, preferably an ampoule, is accommodated or can be accommodated in the receiver. The conveying mechanism may comprise a plunger which can be displaced in the product container and a plunger drive. The housing is made up of a first housing shell and at least a second housing shell, which are joined to one another in a watertight fit by means of a seal. The sealing action is based on a pressing contact of the seal. This results in a self-sealing connection of the housing shells. The housing forms a watertight case for components of the administering device that are sensitive to moisture, preferably for all moisture-sensitive components of the device, in particular the driver mechanism, as well as for a visual, acoustic or vibrating display, an operating mechanism and similar. The first housing shell or the second housing shell may be integral, i.e. made in a single piece by a moulding process. However, the first housing shell or the second housing shell comprises or comprise several parts, in which case the several parts are then joined to one another in a watertight fit if they respectively constitute a wall region of the watertight case formed by the housing.

The word "or" as used in this application, i.e. in the claims and the description, should always be construed in the usual logical sense as meaning "and/or", except where it is obvious from the respective context that it is intended to have a restrictive meaning in the sense of "and" or "either or".

For the purpose of the invention, the seal has an elastic sealing lip, which establishes the pressing contact with the first housing shell. In the extreme situation, the sealing lip alone already constitutes the seal. By preference, however, the seal is a moulding made from an elastic material, on which the sealing lip is formed as a protuberance of the same material. In a preferred embodiment, the sealing lip is made from an elastic material and is moulded onto a base body of non-flexible or significantly less flexible material.

In a preferred embodiment, the first housing shell has a seal gap, into which the sealing lip is pressed so that the pressing contact is exerted in the seal gap. Although less preferable, the sealing effect of the sealing lip may be achieved by mounting the sealing lip as an elastically bendable resilient tongue rather than one obtained by pressing it into a seal gap. The sealing lip can be pressed into the seal gap so that its shape springs elastically inwards, i.e. acts as a bent tongue in the gap. In one particularly preferred embodiment, in the fitted state, it is compressed, i.e. the material is elastically compressed, and clamped between mutually facing walls of the seal gap.

The seal proposed by the invention based on the sealing action of a sealing lip places less stringent requirements on the dimensional stability of the housing shells. When the sealing lip is pressed into a seal gap of the first housing shell, in the preferred manner, there is no longer any need to fear manufacturing inaccuracies in the first housing shell to a degree likely to impair the sealing action, because the sealing action essentially depends only on the manufacturing accuracy of the seal gap and, to a lesser degree, the manufacturing accuracy of the sealing lip. The width of the seal gap, which is crucial to the sealing effect, is shorter than the length and the width of the first housing shell in the joining region by a multiple. Accordingly, the manufacturing tolerance for the gap width is also significantly lower than the manufacturing tolerances for the dimensions of the first housing shell as such, although it is decisive with regard to the design of the sealing ring in the form of an O-ring seal. If the sealing lip is pressed into a seal gap, the sealing effect increases as the ambient pressure decreases. The seal is therefore optimally adapted to the usual low operating pressures which occur in day to day use at high air humidity, under the shower or when swimming. The decrease in the sealing effect as the ambient pressure rises is of less importance because nominal pressure increases can occur only during diving. The seal proposed by the invention is therefore optimally adapted to the prevailing conditions and not to extreme conditions which occur only rarely or not at all. In order to guarantee a reliable sealing effect even at higher operating pressures, the sealing lip is pressed into the seal gap in such a way that the pressing force acting on it, i.e. the pressing force acting in the contact surfaces between the sealing lip and the seal gap, is greater than the highest operating pressure which can be expected during service. To adapt to more pronounced increases in ambient pressure, the seal system may also incorporate a separate O-seal sealing the housing shells with respect to one another in addition to the sealing lip. In preferred basic embodiments, the sealing lip is perfectly sufficient on its own.

The second housing shell may be a simple cap, for example a screw-on cap, which closes off an access opening formed in the first housing shell to provide a battery compartment, for example, in a watertight manner. In preferred embodiments, the second housing shell is a housing cover or a housing base. At its end facing the second housing shell, therefore, a large area of the first housing shell is open. In embodiments of this type, the opening closed off by the second housing shell can be used as a means of introducing the components that are accommodated in the housing during assembly of the administering device, for example the driver mechanism.

The connection between the housing shells may be such that the user is able to release it without difficulty, as is the case with a cover for a battery compartment, for example. By preference, however, the housing shells are connected to one another in such a way that they can not be released from one another without force. For this purpose, the housing shells are preferably also connected to one another by a material join, in addition to the self-sealing connection afforded by means of the sealing lip, for example they are adhered or pressed against one another at another point so that they can not be released.

In a preferred embodiment, the second housing shell has a support structure, which is dimensionally stable or at least more dimensionally stable than the sealing lip. Preferably, the seal surrounds the support structure across at least a major surface region of the support structure. It is also of advantage if the seal for the support structure has an outer sheath. The soft sheath additionally acts as a damping means to prevent impact stress. To obtain a firm connection between the seal and support structure in the preferred manner, it is of advantage if the seal engages round the support structure and even better if it engages behind the support structure. Not only is the support structure able to strengthen the seal and keep it in shape, so to speak, it may also act as a support for the sealing lip in addition to or as an alternative to this function, by supporting the sealing lip at its end remote from the first housing shell.

The support structure and the seal are preferably joined to one another in a form fit, for example by the engagement round or the engagement behind the support structure mentioned above or by means of some other formed elements. In addition to the form-fitting connection or instead of it, the support structure and the seal system may also be joined to one another in a non-positive arrangement or by a material join. In particularly preferred embodiments, the support structure and the seal are connected to one another by a material join, preferably directly, i.e. without material to impart a material joint such as adhesive, for example.

In particular, the seal may be a plastic injection-moulded seal. If the second housing shell incorporates said support structure, the support structure and the seal may advantageously be made by a two-component injecting moulding process, in which case the seal is preferably injected onto a pre-moulded support structure or a pre-moulded support structure in the form of an insert part around which the material of the seal is injected. Of particular advantage during the two-component injection moulding process is the fact that a joint based on a form-fit, a non-positive fit or a material fit can be obtained for a dimensionally stable support structure in the form of a hard component, whilst the seal is produced as a soft component. In particular, this obviates the need to use extra adhesion-imparting materials, for example an adhesive.

Although the seal may be made from natural rubber, it is preferably moulded from a synthetic polymer, preferably a thermoplastic elastomer. In preferred embodiments in which the material of the sealing lip also forms a viewing region of the housing, the seal including sealing lip is advantageously made from a UV-resistant material. In a particularly preferred embodiment, the material has a hardness of 55 Shore A.

In preferred embodiments, an end face of the first housing shell and an end face of the second housing shell lie axially facing one another and preferably may be in contact with one another. The sealing lip preferably projects axially beyond the end face of the second housing shell and preferably stands proud of the relevant end face. The seal gap is advantageously formed in the first housing shell so that it opens at the relevant end face of the first housing shell and the opening of the seal gap of the sealing lip lies axially opposite by reference to the end faces. Such a geometry makes it easier to assemble the housing shells and in particular makes it easier to press the sealing lip into the seal gap.

Although the sealing lip is preferably a constituent part of a housing base or a cap of the housing, it may instead in principle be a constituent part of a housing shell which already forms a case of the housing. In such embodiments, the base of the cap is preferably provided with the seal gap described above.

Advantageous features and combinations of features are also described in the dependent claims. The features described above and those defined in the dependent claims and their combinations are mutually complementary and interchangeable.

An example of an embodiment of the invention will be explained below with reference to the appended drawings. Features which become apparent from the embodiment described as an example advantageously supplement the subject matter of the claims, each individually and in every combination of features, as do the embodiments described above.

Figure 1:
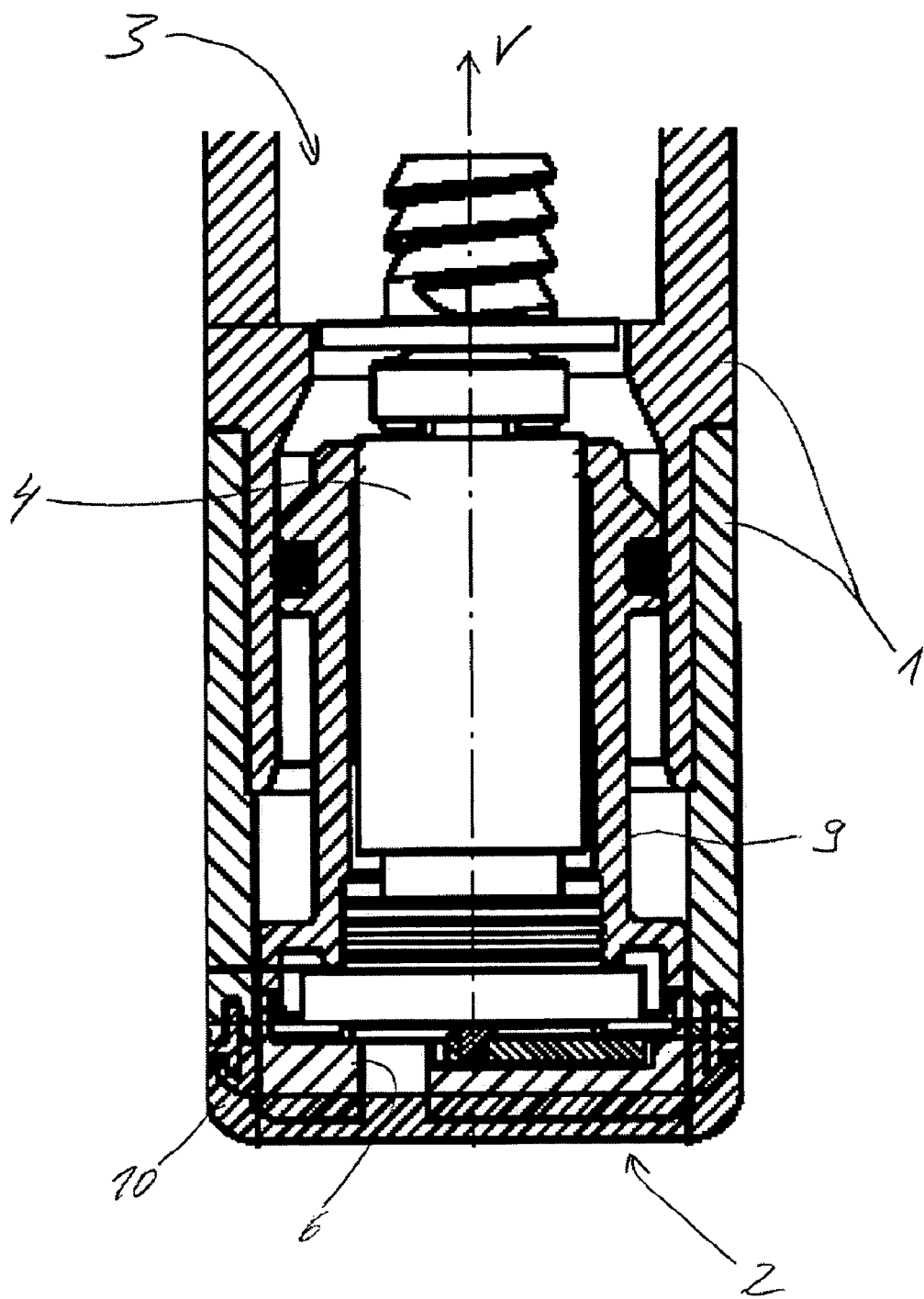
FIG. 1 is a longitudinal section showing part of an administering device.

FIG. 1 is a longitudinal section illustrating a part of an administering device. The administering device is an infusion device for infusing insulin, for example. The infusion device is compact and lightweight so that it can easily be carried in or under the clothing. Apart from the characterising features proposed by the invention, the infusion device may correspond to standard infusion devices used for self-administration, for example insulin pumps.

The infusion device has a housing comprising a first housing shell 1 and a second housing shell 2, which, in the joined state illustrated, form a watertight case for moisture-sensitive components of the infusion device. Housing shell 1 specifically forms a receiver 3 for a product container, which is preferably an ampoule, filled with a product to be administered, for example insulin, of the type used for the treatment of diabetes or other treatments where the patient administers the relevant drug himself. In FIG. 1, the receiver 3 is empty, i.e. there is no product container inserted. The first housing shell 1 also encloses a driver mechanism 4, by means of which the product can be conveyed out of the product container. In particular, the driver mechanism 4 may be a plunger driver with a plunger which can be moved in the product container in a forward drive direction V and a drive mechanism for driving the plunger forward.

The housing shell 1 forms the side wall of the housing 1, 2, but is open at a bottom end face across its entire internal cross-section. The components to be disposed in the housing 1, 2, in particular the driver mechanism 4, can be introduced into the housing shell 1 through the resultant opening and fitted during assembly of the infusion device. Housing shell 2 closes the terminal opening of housing shell 1 in a watertight arrangement and in the connected state forms the base of the housing 1, 2.

The housing shell 2 comprises several parts, although the several parts are connected to one another to form a solid unit. Housing shell 2 comprises a dimensionally stable support structure 6 and a seal 10, which form the base of the housing 1, 2, and a holder 9 projecting from the support structure 6 into the housing shell 1 for the for the driver mechanism 4. The support structure 6 and the holder 9 are formed from the same dimensionally stable, curable plastic material. The seal 10 is injection-moulded onto the support structure 6. The seal 10 is made from a thermoplastic elastomer. The support structure 6 and the seal 10 are joined to one another in a form fit and by a material join. The support structure 6 and the holder 9 are joined to one another in a form fit and a non-positive fit. The support structure 6 is formed by an injection moulding process and the seal 10 is injected around it. Accordingly, due to the multi-component injection mould process, a particularly solid joint is obtained between the support structure 6, which constitutes a hard component, and the seal 10 in the form of a soft component.

Figure 2:
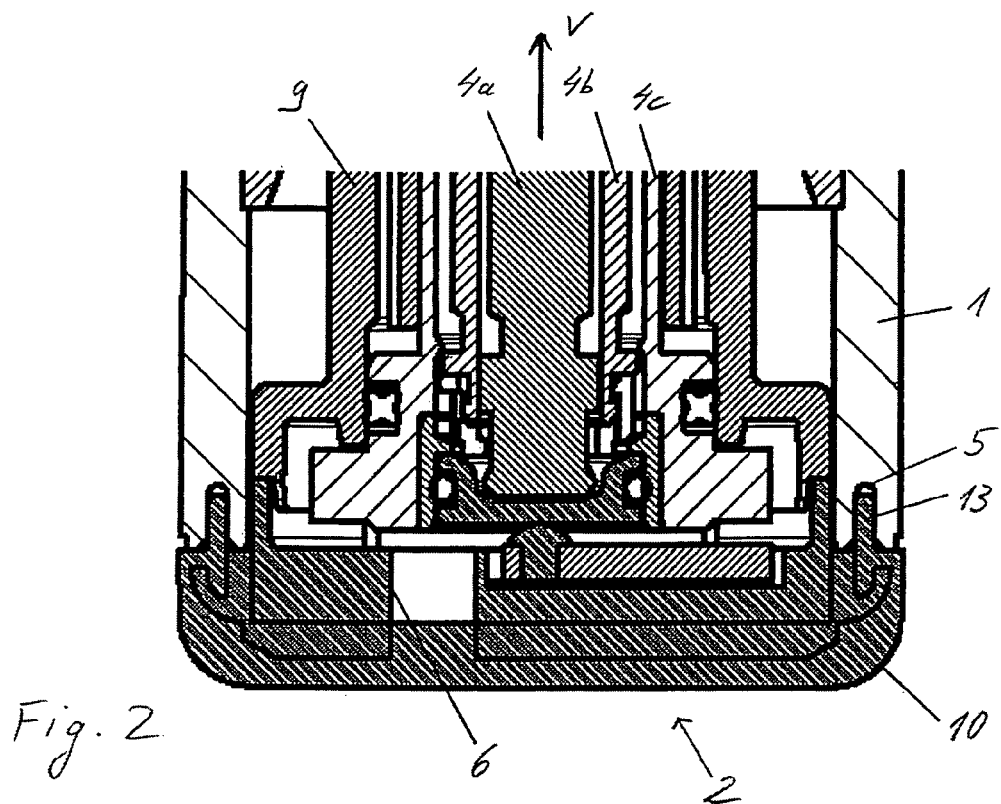
FIG. 2 shows the region where two housing shells of the administering device are joined.

FIG. 2 illustrates the base region of the injection device, in particular the region where the housing shells 1 and 2 are joined, as well as an example of a driver mechanism 4. The driver mechanism 4 comprises a central plunger rod 4a, a central drive member 4b coaxially surrounding the plunger rod 4a and an outer drive member 4c coaxially surrounding the drive member 4b. The drive members 4b and 4c are provided in the form of drive sleeves. The plunger rod 4a and the central drive member 4b engage by means of a thread so that the plunger rod 4a is moved axially in the forward drive direction when the drive member 4b is driven in rotation. The drive members 4b and 4c engage with one another by means of another thread. Together, the plunger rod 4a and the drive members 4b and 4c form a telescopic drive unit for the plunger and, in conjunction with the plunger, the driver mechanism 4. Examples of such telescopic driver mechanisms are described in patent specifications U.S. Ser. No. 09/403,443 and EP 0 991 440 B1, which are included herein by way of reference.

The drive member 4c is axially supported on the support structure 6 in the direction opposite the forward drive direction and, in the embodiment illustrated as an example, the drive member 4c is supported on an axially protruding projection, formed in the central region of the support structure 6. The drive member 4c is supported on the holder 9 in the forward drive direction V and transversely thereto in the radial direction.

The housing shells 1 and 2 are joined to one another by means of a self-sealing connection. The self-sealing connection exists directly between the housing shell 1 and a sealing lip 13 of the seal 10. The sealing lip 13 projects axially from an end face of the seal 10 facing the housing shell 1, i.e. vertically. A seal gap 5 is formed in the housing shell 1 at its terminal end, which opens at the end face of the housing shell 1 facing the end face of housing shell 2. The seal gap 5 projects axially out from its orifice in the end face into the housing shell 1. The seal gap 5 and the sealing lip 13 are each formed so that they extend continuously around a central axis pointing in the forward drive direction V and are in axial alignment with one another. The sealing lip 13 is pressed into the seal gap 5 and establishes a pressing contact with each of the oppositely lying, mutually facing side walls of the seal gap 5. The relevant side walls of the seal gap 5 are parallel with one another and with the forward drive direction V of the driver mechanism 4.

Figure 3:
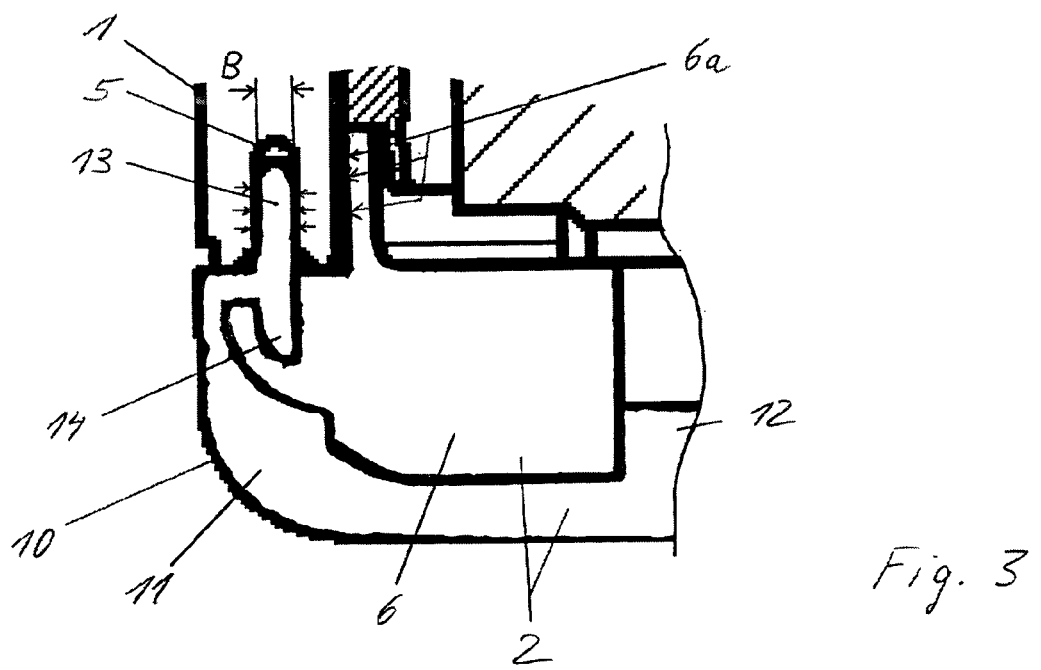
FIG. 3 shows a detail of the joining region.

FIG. 3 is a diagram illustrating a point of the self-sealing connection on a large scale than FIG. 2. The hatching of the support structure 6 and the seal 10 have been omitted solely for the sake of clarity.

The seal gap 5 has a gap width B of a few tenths of a millimetre extending all around it. The manufacturing tolerance of the seal gap 5 with respect to the gap width B is correspondingly small. The manufacturing tolerance is smaller than the standard dimension by at least one order of magnitude, i.e. by at least a factor of 10. If the standard dimension for the gap width B is 0.2 mm, for example, the tolerance is therefore ±0.02 mm, for example. The sealing lip 13 has over size in comparison to the gap width B, so that it is compressed in the narrower seal gap 5 when pressed in and sits in pressing contact with the side walls of the seal gap 5. The pressing pressure bearing on the contact surfaces of the sealing lip 13 is indicated by several small arrows.

The seal 10 is disposed on the external face of the support structure 6 and surrounds the support structure 6, lying tightly against it like a sheath. Consequently, the seal 10 not only forms the sealing lip 13 but also has a shell region 11 which forms a bottom face of the housing shell 2 and hence the housing 1, 2. The shell region 11 is so thick and the material of the seal 10 so soft that the seal 10 also acts as a damping means and anti-slip means on the bottom face of the housing 1, 2. The shape of the seal 10 is akin to that of a flat pan. It extends from the bottom face across its outer peripheral region as far as a top face of the support structure 6 and engages round an outer peripheral edge on the top face of the support structure 6. To obtain an even firmer form fit, it not only engages round the support structure 6 but also engages behind the support structure 6 by means of an anchoring element 14 lying axially opposite the sealing lip 13 and projecting towards the bottom face. Accordingly, the support structure 6 has a recess on its top face, in which the anchoring element 14 is accommodated. In the embodiment illustrated as an example, the recess in the support structure 6 is provided in the form of a peripheral groove and the anchoring element 14 on the seal 10 is provided in the form of a peripheral protuberance similar to the sealing lip 13. Since the seal 10 engages round the support structure 6 and advantageously also engages behind it, a non-positive fit is also obtained between the support structure 6 and the seal 10 in addition to the form fit, because the plastic material from which the seal 10 is made confines the support structure 6 after the injection process. In a central region, the support structure 6 also has an orifice or recess, into which the seal 10 projects by means of a base 12, which completely fills the recess or orifice of the support structure 6. As a result, an additional anchoring is obtained for the support structure 6 in the central region of the seal 10.

The support structure 6 not only acts a support frame for the seal 10 as such, but also as an axial support for the sealing lip 13. To this end, the support structure 6 extends outwards beyond the seal gap 5. The support structure 6 therefore also serves as a stop, by means of which housing shell 2 sits in contact with housing shell 1 in the axial direction in the connected state, so that the axial position of housing shell 2 relative to housing shell 1 is exactly defined when in contact. The relevant end face of the support structure 6 lies opposite the part of the end face of the housing shell 1 which internally adjoins the orifice of the seal gap 5. The part of the end face of housing shell 1 externally adjoining the orifice of the seal gap 5 lies opposite an end face of the seal 10 and is preferably pressed into this end face of the seal 10 with a slight pressing pressure.

In addition to the pressed joint obtained by means of the sealing lip 13, the housing shells 1 and 2 are also non-detachably connected to one another by means of a material join. The material join is obtained by bonding. The region of the material join 6a, which in the embodiment illustrated as an example is a bonded region, extends peripherally along a casing internal face of the housing shell 1 adjoining the end face of the housing shell 1 and a casing external face of the support structure 6 adjoining it in a non-positive fit.

Figure 4:
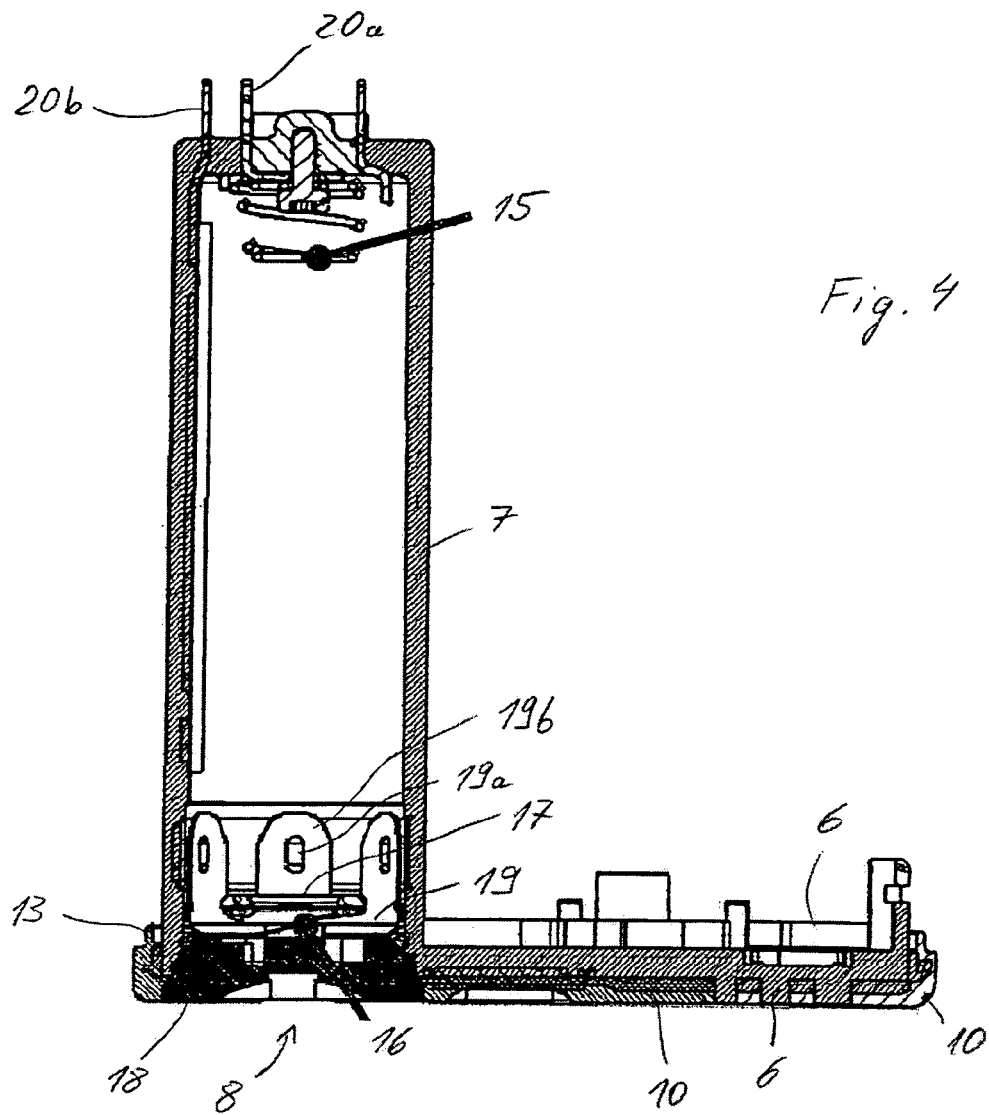
FIG. 4 shows one of the housing shells with a battery compartment.

FIG. 4 is a diagram in section illustrating the compartment 7 of a device for injecting or infusing a product, in which a power source, e.g. a cylindrical battery, can be inserted. The compartment 7 is manufactured in a single piece with the bottom part of the device, e.g. during the injection moulding process. It its bottom face, the compartment 7 has an access opening 8, by means of which the power source can be inserted in the compartment and removed from the compartment. This option is provided because the device may be designed for a longer service life than the power source, which will then have to be replaced whenever necessary. The shape of the compartment 7 for the power source is such that the compartment 7 affords a reliable lateral guiding action for the power source, making it easy to insert the power source.

The access opening 8 can be closed by means of a cover 18. This cover 18 is designed to close off the compartment 7 rendering it watertight because penetration of the compartment by moisture can cause the power source to short-circuit. In order to obtain a high quality seal, the cover 18 is provided in the form of a screw-on cap and also has a sealing ring 26, which is pressed against an internal wall of the compartment 7 when the cap 18 is screwed on.

Disposed at the top end of the compartment 7 is a first contact 15, against which one terminal of the power source can be pushed. The contact is provided in the form of a contact spring 15, which means that it can be elastically compressed when biased by the power source in its insertion direction and spring back into its initial position when no longer biased. The contact spring 15 itself may form an electric down conductor or is connected to a down conductor 20a. The power source is connected to a consumer, e.g. a driver mechanism, by means of this down conductor. In order to establish a connection with the consumer, which as a rule lies outside the compartment 7, the down conductor 20a is run through the external wall of the compartment 7 or is embedded in it during moulding or inserted during the process of injection moulding the compartment 7, in such a way that a terminal piece of the down conductor 20a stands proud of the outer wall of the compartment 7, enabling a connection to a consumer to be plugged in, for example. The first contact spring 15 together with its holder may likewise be embedded in the wall of the compartment 7 during moulding. It could just as easily be secured in the compartment 7 by means of a screw, adhesive, by welding or by similar means. It would also be conceivable for the first contact spring 15 to be made as a single component together with the down conductor, in which case it forms the cover or a part of the cover of the compartment 7 and is inserted in the body of the compartment 7, e.g. bonded.

Likewise disposed on the compartment 7, standing proud of the surface, is another down conductor 20b, which is connected to a second contact spring 16. Like the first contact spring 15, this second contact spring 16 may lie in the compartment 7. By preference, the second contact spring 16 lies in the compartment 7 opposite the first contact spring 15, i.e. the mid-points of the two contact surfaces of the contact springs 15, 16 lie essentially on an axis, e.g. the longitudinal axis of the compartment 7 and extend essentially parallel with one another. The directions in which the first contact spring 15 and the second contact spring 16 can be biased are therefore opposite one another. The spring path of the two contact springs 15, 16 is therefore essentially the same. It is particularly preferable if the second contact spring 16 is secured to the cover 18, as is the case in the embodiment illustrated as an example.

The clearance distance between the contact surface of the first contact spring 15 and the contact surface of the second contact spring 16 is shorter than the length (meaning the distance between the foremost tip of the terminal and the foremost tip of the opposite terminal) of the power source which can be positioned between the contact surfaces. By preference, it is smaller than the length of the power source plus the spring path of one of the contact springs 15, 16. When the power source is biased in the longitudinal direction, this will ensure a reliable contact between the terminals of the power source at all times, even if the power source has a moment of inertia which is different from that of the device or parts of it, due to its relatively high specific weight.

In order to connect the second contact spring 16 via the down conductor 29b to the consumer, a tape of conductive material is attached to a major part of the length of the compartment 7, on or in its internal wall, in the embodiment illustrated as an example here, and is connected to a ring of likewise conductive material provided in the peripheral direction in the bottom region of the compartment 7. When the cap is screwed on, this ring is in contact with indentations 19a of a crown-shaped connecting element 19, which is made from conductive material and is mounted on the cap 19. This connecting element is in turn connected to the second contact spring 16 so that when the power source is inserted, power can be transmitted from the second contact spring 16 via the connecting element 19 and the down conductor 20b to the consumer.

The down conductor 20b need not necessarily be provided in the form of a tape of conductive material, as a wire, with or without insulating sheath, a thin strip or any other connecting geometry would also fall within the scope of this invention. Similarly, the down conductor need not necessarily run through the compartment 7 and instead, a run could be moulded entirely in the wall of the compartment 7 or a run along the external wall of the compartments 7 would also be conceivable. It is merely necessary to ensure that the entire down conductor 20b is disposed inside the sealed housing of the device and a reliable connection to a consumer can be established. Equally, the ring disposed in the peripheral direction mentioned above need not necessarily be a closed ring. As long as it is guaranteed that the connecting element 19, which will be described in more detail below, can reliably establish a contact with the down conductor 20b when the cap 18 is fitted, it may be provided in the form of a part-ring, the extension of the tape itself or a dot-shaped contact point or any other shape of contact surface. In order to establish the requisite contact between the connecting element 19 and down conductor 20*b* reliably, the last part of the down conductor 20*b* may also be provided in the form of an increasing material thickness or may project into the compartment 7 due to the shape imparted to the internal wall of the compartment 7 in the region of the connecting element 19.

Figure 5:
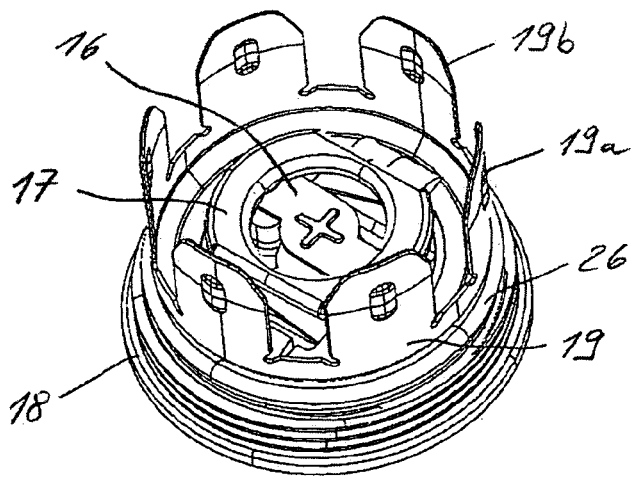
FIG. 5 shows a contact spring integrated in a cover of the battery compartment.

The above-mentioned cap 18 is illustrated in detail in FIG. 5. It essentially consists of a base body with an external thread. This thread fits exactly in the internal thread formed in the access opening 8 of the compartment 7. In the screwed-on state, the cap 18 closes off the compartment 7, and preferably closes it off so that it is watertight. The base body has a side, which is not visible here, which forms the external face of the device in the screwed-on state and may have a locating feature for stowing a cap tool to enable the cap 18 to be firmly pulled on. Attached to the oppositely lying side of the base body, i.e. the side which lies in the interior of the compartment 7 when the cap 18 is screwed on, is the above-mentioned connecting part 19. It may be attached by means of a screw or rivet connection, a bonded or welded connection, a clamp or some other mechanical connection or any other type of connection that will guarantee a reliable connection of the connecting element 19 to the cap 18.

A sealing ring 26 may be inserted between the cap 18 and the connecting element 19 to provide additional sealing. This sealing ring 26 is squashed in the compartment 7 when the cap 19 is firmly screwed on and thus improves the sealing action of the screw connection.

In the embodiment illustrated as an example here, the connecting element 19 is crown-shaped, i.e. several extensions 19*b* standing vertically proud of the base body are disposed in a circle about the mid-axis of the cap 18. The extensions 19*b* are connected to one another in the region of the connection with the cap 18 and are also spaced uniformly apart. The extensions may have a simple rectangular shape, with oblique ends, as is the case in the embodiment illustrated as an example, or may be semi-circular, for example. At their top part, i.e. remote from the cap 18, they may have indentations 19*a*, which are formed by indenting the material of the connecting element 19, for example. The diameter of the circle formed by the extensions 19*b* is large enough for the power source to be engaged by the extensions 19*b* in this region.

Disposed in the interior of the crown formed by the connecting element 19 is the second contact spring 16. As with the first contact spring 15, it may be provided in the form of a leaf spring, coil spring, helical spring or bending spring. It stands proud of the cap 18 in the direction towards the interior of the compartment 7 and is able to spring inwards in the opposite direction, i.e. against the cap 18. The second contact spring 16 is conductively connected to the connecting element 19. This can be achieved using an appropriate connection between the second contact spring 16 and connecting element 19, e.g. a soldered connection, although it would also be conceivable for the connecting element 19 and the contact spring 16 to be made as a single part, in which case it may be made from a thin metal sheet, for example, by an appropriate punching and forming process.

As described above, the power source is connected to the down conductor 20*b* via the second contact spring 16 and the connecting element 19. If, as is the case in the embodiment illustrated as an example here, the contact is established between the connecting part 19 or its extensions 19*b* and a ring-shaped metal tape of the down conductor 20*b*, it may be of advantage to bias the extensions 19*b* with a radial pre-tensioning force, preferably a pre-tensioning force that is directed radially outwards. This pre-tensioning, either alone or in conjunction with the power source accommodated in the crown formed by the extensions 19*b*, ensures or ensure a reliable contact.

Instead of the crown illustrated, the connecting element may have only one extension 19*b* or any number of extensions 19*b*. If a circle of tape in the interior of the compartment 7 is used as the counter-contact, it will still be possible to establish a reliable contact with only one extension 19*b*. However, the contact of the down conductor 20*b* could also extend over only a part of the periphery of the internal wall of the compartment 7 or could be provided in the form of a tape or strip. In the latter case, a reliable contact can still be guaranteed if the connecting element 19 is provided in the form of a closed circle. The decisive factor is that when the cap 18 is firmly screwed on, a contact always exists between the connecting element 19 and the down conductor 20*b*, by means of which power can be transmitted to a consumer.

In order to prevent failure or incorrect functioning of the device due to incorrect positioning of the power source in the compartment 7, a mispoling protector 17 may be provided. This mispoling protector 17 is made from a non-conducting material and is applied, e.g. bonded, directly to one of the contact springs 15, 16. The mispoling protector may basically be of any shape, but preferably has an annular shape or the shape of a flat, circular disc. This being the case, the thickness of the ring or circular disc is big enough for the projecting opposite terminal, in the case of a battery for example, to project through the hole in the middle of the ring or disc up to the second contact spring 16. If the battery is inserted incorrectly, the mispoling protector 17 must reliably prevent contact between the contact spring 16 and the flat terminal.

Figure 6:
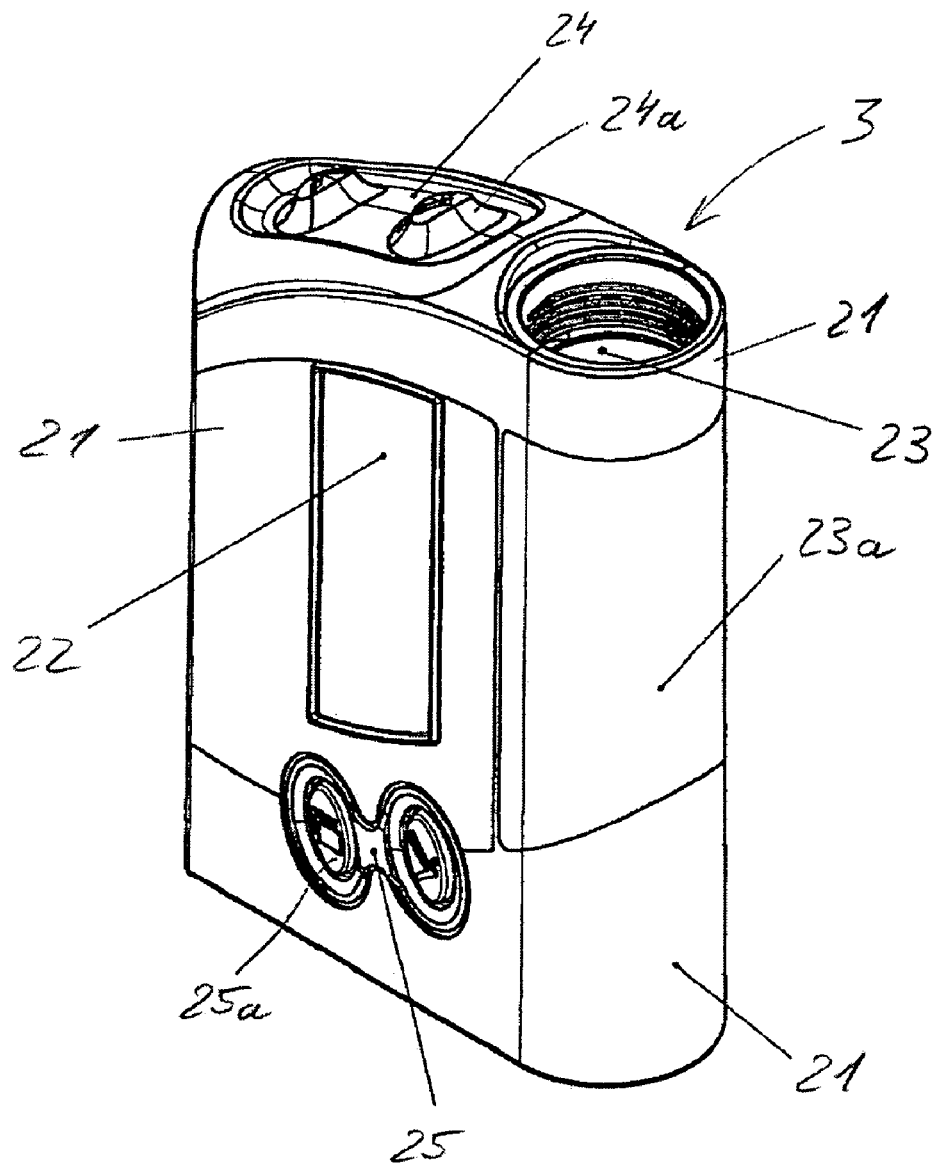
FIG. 6 is a perspective view of the other of the housing shells.

FIG. 6 illustrates the first housing shell 1 in a state immediately after production before the infusion device is assembled. Housing shell 1 forms the side walls and the major part of an upper terminal wall of the housing 1, 2. The shell structure 21 is oval in cross-section with two parallel side walls and two cylindrical, in the embodiment illustrated as an example circular cylindrical, side walls connecting the parallel side walls. The oval hollow cross-section is completely open at the bottom face, where it is closed off by the second housing shell 2 when the infusion device is in the assembled state, as described above. In addition to the open bottom face, the housing shell 1 has only one other opening, namely an opening of the receiver 3 remote from the bottom face. The product container can be inserted in the receiver 3 through the opening. The opening can be closed by means of a screw cap and O-sealing ring, rendering it watertight. The housing shell 1 is watertight with the exception of the two openings.

Insofar as the housing shell 1 forms the external wall of the housing 1, 2, it comprises a shell structure 21, two transparent wall regions 22 and 23*a* and two flexible wall regions 24 and 25. The wall region 22 is a display window. The wall region 23*a* forms a larger part of the external wall of the receiver 3 and the wall regions 24 and 25 screen two control fields, each with two control elements. The control elements are push buttons. The wall regions 24 and 25 each have an indentation for each control element, respectively an indentation 24*a* and 25*a*. The shape of the indentations 24*a* and 25*a* is adapted to the shape of the respective control element. A three-dimensional structure is imparted to the wall regions 24 and 25 as a result of the indentations 24*a* and 25*a*, which matches the structure of the respective control field. The control elements behind the wall region 25 are used as a means of controlling a display, for example for retrieving specific information. The control elements behind the wall region 24 are used for controlling the infusion device, for example for selecting a specific bolus. The wall regions 24 and 25 are so flexible that they enable the control elements to be operated without any difficulty.

The shell structure 21 forms a type of skeleton for the housing shell 1. It is made from a plastic material, which is solid and hard enough to provide a dimensionally stable case in spite of having only a slim wall thickness in the range of tenths of a millimetre, which protects the components accommodated in the housing shell 1 from the mechanical stress which can be expected during operation.

The plastic material of the shell structure 21 may be impermeable to light. The wall regions 22 and 23*a*, on the other hand, are made from a transparent plastic material to enable the display to be read and to ensure that the level control of the product container is visible.

The wall regions 22, 23*a*, 24 and 25 fill the openings of the shell structure 21. The wall regions 22 to 25 are intrinsically watertight and are connected to the shell structure 21 along the edge of the respective opening of the shell structure 21 around the periphery in a continuous watertight fit.

The housing shell 1 is made by a multi-component injection moulding process. For moulding purposes, the injection mould used has a cavity matching the shape of the housing shell 1, which is filled with moulding material. The wall regions 22 and 23 are also formed by injection moulding before the shell structure 21 is moulded, and the wall region 22 is made as a flat thin disc. The wall region 23*a* forms a circular tube, which is entirely made from the transparent plastic material and not only forms the transparent wall region 23*a* of the housing external wall but also forms the side wall of the receiver 3 peripherally.

To make the housing shell 1 by the injection moulding process, the wall region 22 and the tube 23 are placed in the injection mould. To make the shell structure 21 by the injection moulding process, fillers are also placed in the injection mould in place of the wall regions 24 and 25, each of which has the same shape as the opening to be formed in the shell structure 21. Once the fillers and the insert parts 22 and 23 have been positioned, the injection mould is closed and the material of the shell structure 21 is injected in. The plastic material of the shell structure 21 is injected around the insert part 22 along its side edge. Around the insert part 23, the injection takes place on both of its end faces across an arcuate region in each case. The plastic material of the shell structure 21 also adjoins the external face of the insert part 23 in two longitudinal strips and is connected to this external face along the two strips, rendering it watertight.

An injection then takes place in the same manner around the wall regions 22 and 23*a*, rendering them watertight, and once the plastic material of the shell structure 21 has cured, the injection mould is opened and the fillers removed. The injection mould is then closed again. In a final step of the injection moulding process, the elastomeric plastic material is injected through nozzles that were previously closed into the cavities in the injection mould produced by the fillers, where it is injected onto the shell structure 21. As a result of the latter injection, a watertight connection is produced, extending continuously along the edge of the respective opening of the shell structure 21. The flexible wall regions 24 and 25 are connected to the respective opening edge of the shell structure 21 in a watertight fit along their outer edge due to a combination of the form fit and the material join. The watertight connection of the transparent wall regions 22 and 23*a* to the shell structure 21 is also essentially based on a material join and form fit between the two plastic materials.

In a preferred variant of the method, the housing shell 2 is produced entirely with one injection mould, with the exception of the insert parts 22 and 23, which are produced beforehand in a separate injection mould or are each produced in a separate injection mould. Once the pre-moulded insert parts 22 and 23 have been placed in the injection mould for making the housing shell 2, the injection mould is closed and the second plastic material is injected around the insert parts 22 and 23. The injection mould then opens and the core of the injection mould together with the shell structure 21 and the insert parts 22 and 23 rotates into a second cavity in the same mould. Before the injection mould closes again, the insert parts 22 and 23 for the next housing shell 2 are placed in the first cavity, which is now free again. Once the mould has closed, the second plastic material is injected around the insert parts 22 and 23 in the first cavity again. In the second cavity, the soft components 24 and 25, i.e. the elastic wall regions, are simultaneously injected. Once the injection mould has opened and the finished housing shell 2 has been ejected from the first cavity and insert parts 22 and 23 have been placed in the first cavity again, the "carousel" starts again.

REFERENCE NUMBERS

1 First housing shell
2 Second housing shell
3 Receiver
4 Conveying mechanism
4*a* Plunger rod
4*b* Drive member
4*c* Drive member
5 Seal gap
6 Support structure
6*a* Region of material join
6*b* Raised area
7 Battery compartment
8 Access opening
9 Holder
10 Seal
11 Shell region
12 Base
13 Sealing lip
14 Anchoring element
15 Contact spring
16 Contact spring
17 Mispoling protector
18 Cap
19 Connecting element
19*a* Projection, indentation
19*b* Extension
20*a* Down conductor
20*b* Down conductor
21 Shell structure
22 Insert part, transparent wall region
23 Insert part
23*a* Transparent wall region
24 Flexible wall region
24*a* Indentation
25 Flexible wall region
25*a* Indentation
26 Sealing ring
B Gap width
V Forward drive direction

The invention claimed is:
1. An administering device for infusing or injecting a product, comprising
a housing comprising
a first housing shell; and a second housing shell, the second housing shell comprising an outer shell and a support structure, wherein the outer shell surrounds at least a portion of the support structure, and wherein the support structure is formed of a material that is harder than the material that forms the outer shell;

a receiver for the product, disposed in the housing; and a conveying mechanism for conveying the product, the conveying mechanism comprising a drive member;

wherein the second housing shell comprises a sealing lip for establishing a pressing contact with the first housing shell such that a watertight seal is formed between the first and second housing shells;

wherein the outer shell is molded onto the support structure or is fixedly connected to the support structure; and wherein the drive member is axially supported on the support structure.

2. The administering device as claimed in claim 1, wherein the sealing lip projects axially out beyond an end face of the second housing shell.

3. The administering device as claimed in claim 1, wherein sealing lip projects radially out from an end face of the second housing shell.

4. The administering device as claimed in claim 1, wherein the second housing shell forms a base of the housing.

5. The administering device as claimed in claim 1, wherein the sealing lip is a fixed constituent part of the second housing shell.

6. The administering device as claimed in claim 1, wherein the outer shell is formed in a single piece with the sealing lip, and the sealing lip protrudes from a face of the outer shell.

7. The administering device as claimed in claim 1, wherein the outer shell is connected to the support structure by means of a form fit.

8. The administering device as claimed in claim 1 wherein the outer shell is disposed on the side of the support structure that faces away from the conveying mechanism.

9. The administering device as claimed in claim 1, wherein a battery compartment is formed in the housing and an access opening for the battery compartment is formed in the support structure, and the outer shell is connected to the support structure around the edge of the access opening so as to be peripherally watertight.

10. The administering device as claimed in claim 1, wherein the outer shell is injection-molded onto the support structure.

11. The administering device as claimed in claim 1, wherein the sealing lip is pressed in the pressing contact with a pressing pressure which is greater than the maximum ambient pressure which can be anticipated during operation of the administering device.

12. Administering device as claimed in claim 1, wherein the outer shell comprises a thermoplastic elastomer.

13. The administering device as claimed in claim 1, wherein the outer shell comprises a plastic injection-molded seal.

14. The administering device as claimed in claim 1, wherein the second housing shell further comprises a holder structure that extends axially into the first housing shell and supports the conveying mechanism within the housing.

15. The administering device as claimed in claim 1, wherein the sealing lip extends axially from an end face of the seal that faces the first housing shell, and the first housing shell comprises an axially extending seal gap adapted to receive the sealing lip.

16. The administering device as claimed in claim 1, wherein the outer shell further comprises an anchor element extending axially from the outer shell in a direction substantially opposite the direction of the sealing lip, and the support structure comprises an axially extending recess adapted to receive the anchoring element.

17. The administering device as claimed in claim 1, wherein the first housing shell is formed of a curable plastic, and the second housing shell is formed of rubber or a thermoplastic elastomer.

18. The administering device as claimed in claim 1, wherein the outer shell engages around the support structure at its edge.

19. The administering device as claimed in claim 18, wherein the outer shell comprises an anchoring element for engaging behind the support structure.

20. The administering device as claimed in claim 19, wherein the support structure comprises a recess on a side thereof facing the conveying mechanism, and the anchoring element is pressed into the recess of the support structure.

21. The administering device as claimed in claim 1, wherein the first housing shell comprises a seal gap into which the sealing lip is pressed to establish the pressing contact.

22. The administering device as claimed in claim 21, wherein the seal gap comprises a gap width of at least 0.1 mm at least in the gap region where the pressing contact is established.

23. The administering device as claimed claim 21, wherein the seal gap in the first housing shell comprises a groove, and wherein an opening of the groove lies in an end face of the first housing shell.

24. The administering device as claimed in claim 21, wherein the seal gap comprises a gap width of at most 0.5 mm or a gap width of at most 0.4 mm at least in a gap region where the pressing contact is established.

25. The administering device as claimed in claim 24, wherein the gap region comprises a gap width of at most 0.3 mm.

* * * * *

UNITED STATES PATENT AND TRADEMARK OFFICE
CERTIFICATE OF CORRECTION

| | | |
|---|---|---|
| PATENT NO. | : 7,931,620 B2 | Page 1 of 1 |
| APPLICATION NO. | : 11/345652 | |
| DATED | : April 26, 2011 | |
| INVENTOR(S) | : Marco De Polo, Philip Etter and Remo Steiner | |

It is certified that error appears in the above-identified patent and that said Letters Patent is hereby corrected as shown below:

Col. 5, Line 24, "for the for the" should read -- for the --

Col. 7, Line 30, "It its bottom" should read -- In its bottom --

Signed and Sealed this
Twentieth Day of September, 2011

David J. Kappos
*Director of the United States Patent and Trademark Office*